US005683888A

United States Patent [19]
Campbell

[11] Patent Number: 5,683,888
[45] Date of Patent: Nov. 4, 1997

[54] MODIFIED BIOLUMINESCENT PROTEINS AND THEIR USE

[75] Inventor: Anthony Keith Campbell, Penarth, United Kingdom

[73] Assignee: University of Wales College of Medicine, Cardiff, United Kingdom

[21] Appl. No.: 270,314

[22] Filed: Jul. 5, 1994

Related U.S. Application Data

[63] Continuation of Ser. No. 820,867, Jan. 22, 1992, abandoned.

[30] Foreign Application Priority Data

Jul. 22, 1989 [GB] United Kingdom ............... 8916806

[51] Int. Cl.$^6$ .................. C12Q 1/66; C12Q 1/00; C07K 14/00; C07H 21/04
[52] U.S. Cl. .................. 435/8; 435/29; 435/4; 530/350; 530/402; 536/23.4; 536/23.5; 536/23.7; 536/23.2
[58] Field of Search .................. 435/188, 189, 435/8, 69.1, 69.7, 7.6, 29, 4; 530/409, 403, 350, 402; 536/23.2, 23.4, 23.5, 23.7

[56] References Cited

FOREIGN PATENT DOCUMENTS 0103469  3/1984  European Pat. Off. .
0137515  4/1985  European Pat. Off. .

OTHER PUBLICATIONS

G.B. Sala–Newbej et al. (1990) Biochem. Biophys. Res. Comm. 172(2):477–482.
Zenno et al. (1990) Biochem. Biophys. Res. Comm. 171(1):169–174.
Casadei et al. (1990) P.N.A.S. 87:2047–2051.
Kobatake et al. (1993) Anal. Biochem. 208: 303–305.
Watkins et al. Biochem J. (1993) 293:181–185.
Sala–Newby et al. (1991) Biochem. J. 279:727–732.
Sala–Newby et al. (Jul. 1992) FEBS 307(2):241–244.
Wood, K.V. et al. (1989, May 12) Science, vol. 244, pp. 700–702.

Li, Bo Liang et al. (1989, Jan.) Proceedings of the National Academy of Sciences, vol. 86, pp. 558–562.
"Site–Specific Mutagenesis of the Clcium–Binding Photoprotein Aequorin", Proc. Natl. Acad. Sci, USA, vol. 83, Nov. 1986, by Frederick I. Tsuji et al., pp. 8107–8111.
"Bioluminescence of the $Ca^{2+}$–Binding Photoprotein Aequorin After Cysteine Modification", Proc. Natl. Acad. Sci, USA, vol. 86, Jan. 1989, by Kouichi Kurose et al. pp. 80–84.
"The Sulfhydryls of Firefly Luciferase Are Not Essential for Activity", Biochemistry, vol. 25, Nov. 7, 1986, by S. C. Alter et al., pp. 1599–1605.
"Mutated Luciferases With Altered Bioluminescence Emission Spectra", The Journal of Biological Chemistry, vol. 249, Jul. 25, by Thomas W. Cline et al., pp. 4668–4669 (1974).
"Hybridization of Bacterial Luciferase With a Variant Produced by Chemical Modification", Biochemistry, (1971) by Meighen, E. A. et al., Chemical Abstract No. 1279d, vol. 101 (22), 4062–8.
"Use of Low Light Image Microscopy to Monitor Genetically Engineered Bacterial Luciferase Gene Expression in Living Cells and Gene Activation Throughout the Development of a Transgenic Organism", New Methods in Microscopy and Low Light Imaging, 1989, SPIE vol. 1161, by W.H.R. Langridge et al. pp. 216–219.
"Measurement of Protein Phosphorylation by Covalent Modification of Firefly Luciferase", Coll. Med., Univ. Biochem. Soc. Trans. vol. 113, 1990, by Timothy M. Jenkins, p. 315 (Chemical Abstract).

Primary Examiner—Lisa B. Arthur
Attorney, Agent, or Firm—Young & Thompson

[57] ABSTRACT

A modified bioluminescent protein responds to different physical, chemical, biochemical or biological conditions to produce light or radiation of altered characteristics when the bioluminescent reaction is initiated. The modified bioluminescent protein may respond to modification thereof, e.g. by covalent modification. The protein may include signal peptides to "target" it. DNA coding for the bioluminescent protein may be altered to include tissue specific promoter or enhancer genes so that the altered DNA acts as reporter gene.

10 Claims, 1 Drawing Sheet

MODIFIED BIOLUMINESCENT PROTEINS AND THEIR USE

This application is a continuation of application Ser. No. 07/820,867, filed Jan. 22, 1992, now abandoned.

BACKGROUND OF THE INVENTION

This invention relates to bioluminescent proteins, in particular it relates to bioluminescent proteins which have been modified, for example by chemical means or by genetic engineering. Such modified bioluminescent proteins, hereinafter referred to as "rainbow proteins", may be used in the detection and quantification of cells, microbes such as bacteria, viruses and protozoa, and substances of biological interest such as substrates, metabolites, intra- and extracellular signals, enzymes, antigens, antibodies and nucleic acids.

Bioluminescence is the oxidation of an organic molecule, the "luciferin", by oxygen or one of its metabolites, to emit light. The reaction is catalysed by a protein, usually known as a "luciferase", or a "photoprotein" when the luciferin is so tightly or covalently bound to the luciferase that it does not diffuse off into the surrounding fluid.

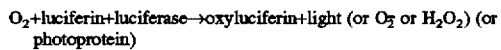

$O_2$+luciferin+luciferase→oxyluciferin+light (or $O_2^-$ or $H_2O_2$) (or photoprotein)

Up to three other substances may also be required to be present in order to generate light, or to alter its colour, and they are as follows:

(a) A cation such as $H^+$, $Ca^{2+}$, $Mg^{2+}$, or a transition metal such as $Cu^+/Cu^{2+}$, $Fe^{2+}/Fe^{3+}$.

(b) A cofactor such as NADH, FMN, or ATP.

(c) A fluor as an energy transfer acceptor.

Five chemical families of luciferin have been identified so far (see FIG. 1 of the attached drawing):

(a) Aldehydes (found in bacteria, freshwater limpet Latia and earthworms).

(b) Imidazolopyrazines (found in Sarcomastigophora, Cnidaria, Ctenophora, some Arthropoda, some Mollusca, some Chordata).

(c) Benzothiazole (found in beetles such as fireflies and glowworms).

(d) Linear tetrapyrroles (found in dinoflagellates, euphasiid shrimp, some fish).

(e) Flavins (found in bacteria, fungi, polychaete worms and some molluscs).

Reactions involving these luciferins may result in the emission of violet, blue, blue-green, green, yellow or red light and occasionally UV or IR light and such emission may or may not be linearly or circularly polarised. Reference is directed to Chemiluminescence principles and applications in biology and medicine, A. K. Campbell, publ. 1988 Horwood/VCH Chichester Weinheim, for further discussion of bioluminescent reactions.

It has now been found that the light emitted from a bioluminescent reaction involving a modified bioluminescent or "rainbow" protein, may be changed in intensity, colour or polarisation. Such a change can then be used in various assays for detecting, locating and measuring cells, microbes and biological molecules.

In this instance, the cell or substance causes a physical or chemical change, such as phosphorylation, to a rainbow protein such as a genetically engineered luciferase, resulting in a change in intensity, colour or polarisation of the light emission. The bioluminescent reaction is triggered by adding, for example, the luciferin, and modification of the luciferase by the cell or substance being measured causes the reaction to emit light at a shorter or longer wavelength. This enables specific reactions to be detected and quantified in live cells, and within organelles or on the inner or outer surface of the plasma membrane, without the need to break them open, and without the need for separation of bound and unbound fractions.

SUMMARY OF THE INVENTION

According to one aspect of the invention there is provided a bioluminescent protein capable of taking part in a bioluminescent reaction to produce light of radiation of altered characteristics under different physical, chemical, biochemical or biological conditions.

The rainbow protein may be produced by the alteration, substitution, addition or removal of one or more amino acids from the end of or within the luciferase or photoprotein. As a result the light emission from the oxyluciferin may be of different colours or different states of polarisation depending on the physical or chemical conditions. A change in colour to another part of the rainbow spectrum may be induced by:

(a) A change in cation concentration such as $H^+$, $Ca^{2+}$, $Mg^{2+}$, or transition metal.

(b) A change in anion concentration such as $Cl^-$ or phosphate.

(c) Covalent modification of the new protein by enzymes causing phospho- or dephosphorylation (including ser/thr, his, and tyr kinases and phosphatases) transglutamination, proteolysis, ADP ribosylation, gly- or glu-cosylation, halogenation, oxidation, methylation and myristilation.

(d) Binding to the rainbow protein of an antigen, an intracellular signal such as cyclic AMP, cyclic GMP, Ip3, Ip4, diacyl glycerol, ATP, ADP, AMP, GTP, any oxy or deoxyribonucloside or nucleotide, a substrate, a drug, a nucleic acid, a gene regulator protein.

(e) Expression of its nucleic acid inside a live cell, as well as its modification or regulation within the cell by gene expression such as promoters, enhancers or oncogenes.

Single or multiple mutations and deletions may be detected in a piece of DNA (eg a PCR product) by linking the "rainbow protein" to one end of the DNA and an energy transfer acceptor or quencher to the other end. Nuclease attack at the mutation will separate the rainbow protein from the acceptor or quencher and thus cause a change in intensity, colour or polarisation of the light emission.

Such alteration, substitution, addition or removal of one or more amino acids may be achieved by chemical means. Alteration of an acid includes alkylation (eg. methylation), phosphorylation and various other covalent modifications of the type outlined herein. Alternatively the nucleic acid coding for the luciferase or photoprotein may be altered by modifying, substituting, inserting or deleting one or more nucleotides such that the resulting protein has gained or lost a site which interacts with the cations, anions, intracellular signal, covalent modification; proteins or nucleic acid to be measured. The insertion or deletion of nucleotides is normally produced by site directed mutagenesis or by opening up the gene with a specific restriction enzyme, inserting or deleting a selected nucleotide sequence and then sealing up of the gene again or using specific primers with the polymerase chain reaction. The nucleic acid is then transcribed to mRNA and this is then translated to form the rainbow protein either inside a bacterial or eukaryotic cell, or in vitro using, for example, rabbit reticulocyte lysate. The new nucleic acid may contain an RNA polymerase promoter such as T7, SP6, or mammalian promoters such as actin, myosin, myelin proteins, MMT-V, SV40, antibody, G6P dehydrogenase, and can be amplified in vitro the polymerase chain reaction. The result is that the rainbow protein can be produced either in a live cell such as a cancer cell, or without cells using enzymatic reactions in vitro. The addition of tissue specific promoter or enhancer sequences to the 5' or 3' end of the DNA coding for the native or altered bioluminescent protein will enable it to be used as a reporter gene and to be expressed specifically in a particular cell or tissue, the expression being detectable by the appearance of a change in light intensity, colour or polarisation.

Another way of producing the DNA for a rainbow protein is to separate into two halves the original DNA for the bioluminescent protein. A piece of DNA or gene is then inserted between the two halves by ligating one half to the 5' end and the other to the 3' end. Alternatively the rainbow protein DNA could be generated using the polymerase chain reaction so that the sense primer had one part of the rainbow protein DNA linked at 5' end and the antisense primer and the other part linked at the 3' end (i.e. antisense). The pieces of DNA or gene of interest, in the middle, could be from two separate genes. For example one could code for am energy transfer protein, the other for a bioluminescent protein. Only when the two are linked together via a peptide (from DNA/RNA) will the rainbow protein be generated and a shift in colour occur. The energy transfer protein could be any fluor bound covalently or non-covalently to the protein, for example the green fluorescent protein from Aequorea, Obelia, Renilla or other cnidarians, or the blue or yellow fluorescent protein from luminous bacteria, or a flavoprotein, or a phyobiloprotein. The whole protein or just the fluorescent demain may be used. The bioluminescent protein would be any luciferase for example bacterial, firefly, glowworm or copepod, or any photoprotein for example aequorin, obelin or a radiolarin such as thalassicollin.

The protein or its DNA or RNA may be incorporated into a live bacterium or eukaryotic cell by using a virus, plasmid, calcium phosphate transfection, electropotation, liposome fusion or membrane pore forming proteins. Once inside, only live cells with the appropriate biochemistry will produce the "rainbow effect". By incorporating the "rainbow protein" gene into an embryo, oocyte, sperm, seed or seed seeding a transgenic animal or plant may be produced, enabling gene expression, cell regulation, drug action, or cell damage to be located and measured in individual organs using the "rainbow effect". These new organisms may also be used in home aquaria, on aeroplane runways, as safe lights at sea, and as house plants.

The rainbow protein may also be incorporated in a different part of the cell by chemical means or genetically engineering the protein to contain a signal peptide which locates it to the inner or outer surface of the plasma membrane or within a particular intracellular organelle (e.g. peroxisome, mitochondrion, chloroplast, endoplasmic reticulum, golgi, secretory vesicle, nucleus or endosome.

Addition of a signal peptide, either chemically or by genetic engineering, will enable the normal or altered luciferase or photoprotein to be targetted into a specific organelle within the cell, or onto the inner or outer surface of the plasma membrane. For example the sequence Met Leu Ser Arg Leu Ser Leu Arg Leu Leu Ser Arg Tyr Leu Leu (SEQ ID No. 1) at the N terminus will locate the bioluminescent protein in the mitochondria, and Lys Lys Ser Ala Leu Leu Ala Leu Met Tyr Val Cys Pro Gly Lys Ala Asp Lys Glu (SEQ ID No. 2) on the N terminus will target the protein to the endoplasmic reticulum, a Lys Asp Glu Leu (SEQ ID No. 3) sequence at the C terminus retaining it there.

The initial luciferase or photoprotein or its gene may come from any of the known chemistries in bioluminescence (see FIG. 1) or from the wide range of uncharacterised luminous organisms from more than 700 genera representing at least 16 phyla. The luciferin may be synthesised chemically and added to the biological reaction or cell to generate light. Aternatively, the gene coding for the enzymes responsible for making the luciferin may be linked to the "rainbow protein" gene so that the artificial operon or fusion gene expresses both rainbow protein and makes luciferin in the live cell from normal cell constituents such as amino acids.

According to a second aspect of the invention there is provided a method of producing a bioluminescent protein by altering, substituting, adding or deleting one or more amino acids to the protein by chemical means or by genetically engineering the nucleic acid coding for the protein.

According to a further aspect of the invention there is provided nucleic acid coding for the bioluminescent protein as hereinbefore defined.

The rainbow protein, or the nucleic acid coding for it, may be used in a range of biological investigations; such as:

(a) Detection, location and measurement of microbes (protozoa, bacteria, viruses).

(b) Detection and location of cancer cells.

(c) Measurement of enzymes, intracellular signalling and other turnover reactions in cells or fluids.

(d) DNA and RNA binding assays.

(e) Immunoassay and other protein binding assays.

The rainbow proteins and their parent nucleic acids also may be used in genetic engineering, in the development of transgenic animals, plants and microbes, and in horticulture.

According to yet a further aspect of the invention there is provided the use of a rainbow protein, or the nucleic acid coding for the rainbow protein, for the detection, location or measurement of substances of biological interest such as microbes, cells or biological molecules or reactions therein.

In this aspect, the reaction or substances of biological interest are made to interact with the rainbow protein or its parent nucleic acid. Such interactions include direct or indirect linking such as non-covalent or covalent binding as well as energy transfer processes.

Although the invention has been described above it is to be understood that it includes any inventive combination of the features set out above or in the following description.

Figure 1:
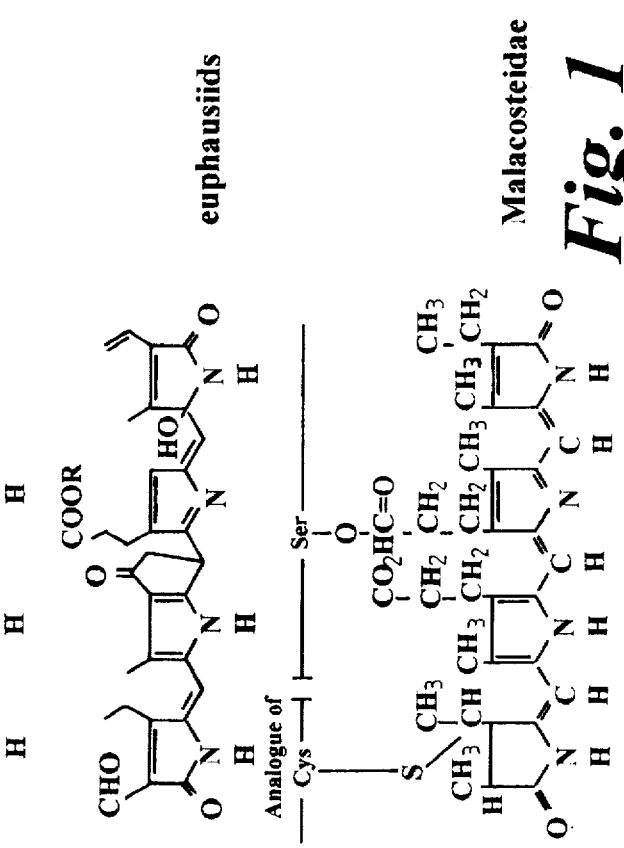
FIG. 1 indicates five chemical families of Luciferin.

The invention may be performed in various ways and will be further described with reference to the following examples:

EXAMPLE 1

Detection of Phosphorylation of a Rainbow Protein

The peptide leu arg arg ala ser leu (SEQ ID No. 4), known as kemptide, or Arg Thr Lys Arg Ser Gly Ser Val Tyr Glu Pro Leu Lys Thr (SEQ ID No. 5) known as malantide was covalently linked to firefly luciferase using disuccinyl suberate at pH8. Addition of 125 ul protein kinase A+cyclic AMP (200 uM)+125 uM ATP caused phosphorylation of the kemptide, now attached to the luciferase. The resulting shift in colour from yellow-green to red at pH 7.8 or from red to yellow-green at pH 6.5, measured as a ratio in a dual wavelength chemiluminometer enabled the rate of protein phosphorylation by the kinase to be assayed, and dephosphorylation induced by phosphatase to be assayed subsequently by the reversal of the ratio.

EXAMPLE 2

Engineering Firefly Luciferase cDNA coding for firefly luciferase was amplified using the polymerase chain reaction (PCR) using 5' sense primers with a T7 RNA polymerase promoter, and 3' antisense primers as follows: Primer code in brackets 5' Sense Primers (105) CACCTAATACGACTCACTATAGGGAGAATGG-AAGACGCCAAAAAC (SEQ ID NO. 6)

(107) AGAACTGCCTGCCGCAGATTCTCGCA (SEQ ID NO. 7)

(110) ATGCTGTCCCGGCTGTCCCTGCGGCTGCTGT-CCCGGTACCTGCTGAAGACGC CAAAAAC (SEQ ID NO. 8)

(111) CACCTAATACGACTCACTATAGGGAGAATGC-TGTCCCGGCTGTCC (SEQ ID NO. 9)

3' Antisense Primers (100) TCTCGCTGAATACAGTTAC (SEQ ID NO. 10)

(106) CCCCAAGCTTAGATCTCTCTGATTTTTCTTGC-GT (SEQ ID NO. 11)

(108) TGCGAGAATCTGCGGCAGGCAGTTCT (SEQ ID NO. 12)

The following firefly luciferase cDNA's were constructed using primers in brackets:

(a) full length (105+100)

(b) −36 bp i.e. missing peroxisomal signal peptide (105+106)

(c) protein kinase A site (Arg Arg Xaa Sec) (SEQ ID NO. 13) in middle of protein (step 1: 105+108 and 107+100; step 2:2 halves from step 1+105+100)

(d) mitochondrial signal at N terminus (step 1:110+100; step 2: step 1 sample+111+100).

The PCR reaction in 50 μl contained 10 mM Tris pH 8.3, 0.01% gelatin, 0.4U Taq polymerase, 2 mM $MgCl_2$, 0.2 mM each dATP, dGTP, dTTP, dCTP, 0.5 μM of each primer, 1 μl DNA (ca 1–100 ng). The reaction, covered with 50 μl mineral oil, was incubated in a Perkin-Elmer thermal cycler for 25 cycles: 94° C. 1 minute, 55° C. 1 minute, 72° C. 2 minutes+5 seconds extension on each cycle, then for 30 minutes at 37° C. with 1U E.coli DNA polymerase (Klenow fragment).

Successful PCR was confirmed by a band on agarose gel electrophoresis. The cDNA was purified by centricon to remove primers, and precipitated in 70% ethanol, 0.7 mM $NH_4$ acetate after extraction with buffered phenol: $CHCl_3$: secondary amyl alcohol (25:24:1). The DNA (0.5–1 μg dissolved in 10mM Tris 0.1 or 1 mM EDTA pH 7.4–7.5) was transcribed in the T7 RNA polymerase in buffer containing 40 mM Tris, pH 7.4–7.5, 6mM $MgCl_2$, 10 mM dithiothreitol, 0.1 mg/ml bovine serum albumin, 2 mM spermidine, 0.5 mM each ATP, CTP, UTP, 0.1 mM GTP, 0.5 mM cap m7 G(5') ppp (5') G, 1000 U RNAsin/ml, 800 U T7 RNA polymerase±2 μC, $^{32P}$UTP for up to 4 hours (1–2 hours optimal), at 37° C. The reaction was stopped in the ice cold phenol: $CHCl_3$: secondary amyl alcohol (25:24:1), and the RNA precipitated in 70% ethanol+0.7M $NH_4Ac$, and stored at −20° C.

The RNA was centrifuged, redissolved in 20 μl 70 mM Tris, 1 mM EDTA pH 7.4–7.5 and 1 μl incubated with 5–10 μl rabbit reticulocyte lysate for 1 hour at 30° C. to synthesize the luciferase. Luciferase, after dilution, 1/100 is assayed for light emission directly in 50 mM tris, 10 mM $MgAc_2$, 0.1 mg/ml bovine serum albumin, 0.1–0.2 mM luciferin, 0.5–5 mM ATP, pH 7.8, or isolated by isoelectric focusing. The mutant (Arg Arg Xaa Sec) (SEQ ID NO. 13) luciferase has a pI of ca 7.1 or 6.8, and the normal luciferase pI ca 6.8. The luciferase with mitochondrial signal also separated from the normal luciferase. On addition of the rabbit reticulocyte lysate containing this altered luciferase it was taken up by added mitochondria, as shown by centrifugation and light emission from the mitochondria and luciferase.

Phosphorylation of the Arg Arg Xaa Sec (SEQ ID NO. 13) containing luciferase with protein kinase A, cyclic AMP (0.2 mM), ATP (0.1–1 mM) pH7, caused the luciferase to change its pI back towards 6.8, and to shift its colour. The RRXS luciferase had a greener light emission than the native luciferase detected using a dual wavelength chemiluminometer with interference filters (maximum transmission ca 545 and 603 mM).

Primers containing kemptide nucleotide sense or antisense sequence (Leu Arg Arg Ala Ser Leu Gly) (SEQ ID No. 4); or malantide Arg Thr Lys Arg Ser Gly Ser Val Tyr Glu Pro Leu Lys Ile (SEQ ID No. 14) were also added either to N or C terminus using a one or two step PCR reaction. These also produced luciferase which could be phosphorylated thereby altering its intensity and colour.

EXAMPLE 3

Preparation of Engineered Aequorin cDNA or genomic coding for the $Ca^{2+}$-activated photoprotein was PCR'd in a similar way to that for firefly luciferase. Using one or two step PCR the protein kinase A recognition peptide kemptide (LRRLALG) or malantide (as Example 2) was added to the N terminus. The mutant aequorin had different kinetic properties enabling protein kinase A to be detected by phosphorylating the altered aequorin (above).

Normal aequorin primers =5' sense TAATACGACTCA CTATAGGGGAGAGAATGGTCAAGCTTTACATCAGA-CTTCGAC, (SEQ ID NO. 15) and 3' antisense GAATTCT-TAGGGGACAGCTCCACCGTA. For insertion (SEQ ID NO. 16) of kemptide at the N terminus the nucleotide sequence equivalent to Leu Arg Arg Ala Ser Leu Gly (SEQ ID No. 4) was attached to the first 15 bases (including ATG) of the 5' end of aequorin. In step 2, the T7 RNA polymerase promoter was added to form the kemptide-aequorin in vitro for in vitro phosphorylation. Genomic aequorin DNA (made by PCR) was at least as active as that made from mRNA by reverse transcriptase PCR.

EXAMPLE 4

Detection of Cancer Cells in Blood

A blood sample (1 ml) is mixed with, a suspension of liposomes containing mRNA coding for a rainbow protein catalysing the benzothiazole reaction c in FIG. 1. This mRNA was produced as follows:

The gene coding for firefly luciferase was first isolated from a cDNA library in E. coli using pCDV1 plasmid primer+Honjo linker containing SP6 RNA polymerase promoter. A nucleotide sequence GCTCGTCTTATTGAA-GATAATGAATATACTGCTCGTTTTGGT representing the phosphorylation site for tyrosine kinase activity of the myc oncogene was inserted at the EcoRI restriction site 30 base pairs downstream from the ATG at the 5' end. The DNA was resealed, recloned and the plasmid insert transcribed by SP6 RNA polymerase in vitro to produce mRNA for the rainbow protein. The original protein produced yellow-green light but the rainbow protein when phosphorylated in the cell produces red light. Thus the presence of cancer cells was detected in blood sample from a leukaemia patient by measuring the ratio of yellow-green (545 nm) to red (603 nm) light in a dual wavelength chemiluminometer.

EXAMPLE 5

Detection of Salmonella

The cDNA for the rainbow protein in Example 4 containing SP6 RNA polymerase promoter was inserted into Salmonella phage. Addition of this phage to Salmonella resulted in expression of the rainbow protein and the generation of red light, enabling as few as 1 bacterium per 20 ml to be detected.

EXAMPLE 6

Detection of HIV RNA

A sample (1 ml) of blood from a patient with AIDS was extracted with 4M guanidium isothiocyanate and the nucleic acid precipitated with ethanol/NH acetate. An oligonucleotide (10 ul, 1 uM) labelled with a rainbow protein generated from the photoprotein obelin was added to 100 ul redissolved RNA at 50° C. and the mixture cooled for 10 minutes at 0° C. The oligonucleotide was specific for a sequence in the HIV coat protein. Binding this to HIV RNA resulted in a shift in the light emission from the rainbow protein from light blue (475 nm) to blue (440 nm). This was detected as a shift in the ratio of light emission at these two wavelengths in a dual photomultiplier chemiluminometer.

EXAMPLE 7

Measurement of Testosterone in Blood

Testosterone carboxyoxime is reacted with the rainbow protein from the photoprotein obelin to form a testosterone rainbow protein conjugate. 5 ul of this containing 1 nmol was incubated with a solution of antibody labelled with fluorescein to testosterone (50 ul) pH 7.4 for 30 minutes in the presence or absence of varying concentrations of standard testosterone. The bioluminescent reaction was triggered by addition of Ca and the ratio of light at 475 nm to 530 nm measured. Increasing the concentration of standard testosterone increased the ratio at 475/530. This procedure could be carried out without the need to separate bound from free antigen.

EXAMPLE 8

Detection of Listeria

A sample of suspect food is boiled to extract DNA. A sense primer to the specific Listeria gene or domain covalently coupled to obelin cDNA+SP6 RNA polymerase promotor and antisense primer covalently coupled to antisense green fluorescent protein (GFP) cDNA is used to amplify the Listeria gene using the polymerase chain reaction. The result is DNA coding for a new rainbow protein and transcribable by SP6 RNA polymerase.

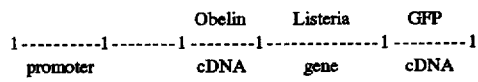

This DNA is transcribed and the mRNA translated using rabbit reticulocyte lysate. Coelenterazine is added to reactivate obelin. The ratio of light at 510/475 nm for rainbow protein versus obelin alone is directly proportional to the amount of Listeria DNA originally present in the food sample. When no Listeria are present the ratio of ratios is 1.

EXAMPLE 9

Measurement of Nucleic Acid Hybridisation by Polarisation

The reaction described in Example 6 was carried out but the light emission was detected in a dual photomultiplier chemiluminometer containing two plane polarised filters with the polarisation planes at 90° to each other. The ratio between the two photomultipliers was related to the amount of HIV RNA present.

EXAMPLE 10

Measurement of Cyclic AMP or Ip3

Using a two step PCR reaction as described in Examples 2 and 3, the cyclic AMP binding domain from the bacterial CAP protein or the Ip3 binding domain of the endoplasmic reticulum receptor was added to the N or C terminus or into firefly luciferase or aequorin. The altered proteins were made in vitro from the PCP DNA product as described in examples 2 and 3 and characterised by activity and colour of light emission cyclic AMP or Ip3. A change in both intensity and colour enabled CAMP or Ip3 to be measured in cell extracts out in living cells. Using an image intensifier a CAMP or Ip3 "cloud" could be visualised in this one cell, Similarly the aequorin or luciferase could be seen within the ER or a mitochondrion if it was first made with an EP or mitochondrial signal attached to it (±KDEL) at the C terminus.

It will be appreciated that the bioluminescent protein may be synthesised from amino acid sequences or using DNA or RNA synthesis techniques, instead of by modification of a protein produced by an organism.

---

What is claimed is:

1. A modified bioluminescent protein selected from the group consisting of firefly luciferase, aequorin and obelin, modified to include an interaction site for a selected analyte, said site being not present in the unmodified protein, wherein the analyte interacts with said interaction site, the bioluminescent protein being reactive in a bioluminescent reaction to produce light, wherein the light is produced having a physical property of a first characteristic when the analyte is interacting with the interaction site, and is produced having a second different characteristic of said physical property when the analyte is not interacting with the interaction site; said interaction site being selected from the group consisting of kemptide covalently bound to the N or C terminus of firefly luciferase, kemptide covalently bound to the N terminus of aequorin, kemptide covalently bound to the N terminus of obelin, malantide covalently bound to the N terminus of aequorin, and an RRXS phosphorylation site at amino acid 217 of firefly luciferase.

2. A bioluminescent protein according to claim 1 for intracellular use, wherein said protein includes a signal peptide for targeting said protein to a specific organelle or site within a cell.

3. A modified bioluminescent protein selected from the group consisting of firefly luciferase, aequorin and obelin, modified to include an interaction site for a substance of interest, said site being not present in the unmodified protein and reactive in a bioluminescent reaction, wherein light emitted in said bioluminescent reaction involving said protein changes depending on the concentration of said substance of interest; said interaction site being selected from the group consisting of kemptide covalently bound to the N or C terminus of firefly luciferase, kemptide covalently bound to the N terminus of aequorin, kemptide covalently bound to the N terminus of obelin, malantide covalently bound to the N terminus of aequorin, and an RRXS phosphorylation site at amino acid 217 of firefly luciferase.

4. Nucleic acid coding for the bioluminescent protein as claimed in claim 1.

5. Nucleic acid according to claim 4, including promoter or enhancer sequences specific to a tissue or substance of interest.

6. Nucleic acid according to claim 4, including a nucleotide sequence coding for an enzyme for producing luciferin.

7. A method of detecting a change in a physical, chemical, biochemical or biological condition, the method comprising:

providing a bioluminescent protein according to claim 1 in a reaction system containing an analyte of interest;

observing whether light of the first and/or second characteristic is produced; and detecting said change based on production of light of said first and/or second characteristic.

8. A method of detecting, locating or measuring a substance of biological interest, the method comprising:

(a) providing a bioluminescent protein according to claim 1 in a reaction system containing an analyte of interest;

(b) analyzing said first and/or second characteristics of the light produced; and (c) detecting, locating or measuring said analyte based on said first and/or second characteristic of the light produced.

9. A method of detecting, locating, measuring a substance of biological interest within a cell which comprises:

introducing into said cell nucleic acid coding for a bioluminescent protein according to claim 1, causing said modified bioluminescent protein to be expressed, causing said bioluminescent protein to take part in a bioluminescent reaction, analyzing said first and/or second characteristics of the light produced; and detecting, locating or measuring said analyte based on said first and/or second characteristic of the light produced.

10. A method according to claim 9, wherein said nucleic acid includes a promoter or enhancer sequence specific to a substance of interest.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 15 amino acids
        ( B ) TYPE: amino acid (D) TOPOLOGY: linear (ii) MOLECULE TYPE: protein (xi) SEQUENCE DESCRIPTION: SEQ ID NO:1:

Met Leu Ser Arg Leu Ser Leu Arg Leu Leu Ser Arg Tyr Leu Leu
1               5                   10                  15

(2) INFORMATION FOR SEQ ID NO:2:

(i) SEQUENCE CHARACTERISTICS:
　　　　(A) LENGTH: 19 amino acids
　　　　(B) TYPE: amino acid
　　　　(D) TOPOLOGY: linear (ii) MOLECULE TYPE: protein (xi) SEQUENCE DESCRIPTION: SEQ ID NO:2:

Lys Lys Ser Ala Leu Leu Ala Leu Met Tyr Val Cys Pro Gly Lys Ala
1               5                   10                  15

Asp Lys Glu (2) INFORMATION FOR SEQ ID NO:3:

(i) SEQUENCE CHARACTERISTICS:
　　　　(A) LENGTH: 4 amino acids
　　　　(B) TYPE: amino acid
　　　　(D) TOPOLOGY: linear (ii) MOLECULE TYPE: protein (xi) SEQUENCE DESCRIPTION: SEQ ID NO:3:

Lys Asp Glu Leu
1

(2) INFORMATION FOR SEQ ID NO:4:

(i) SEQUENCE CHARACTERISTICS:
　　　　(A) LENGTH: 7 amino acids
　　　　(B) TYPE: amino acid
　　　　(D) TOPOLOGY: linear (ii) MOLECULE TYPE: protein (xi) SEQUENCE DESCRIPTION: SEQ ID NO:4:

Leu Arg Arg Ala Ser Leu Gly
1               5

(2) INFORMATION FOR SEQ ID NO:5:

(i) SEQUENCE CHARACTERISTICS:
　　　　(A) LENGTH: 14 amino acids
　　　　(B) TYPE: amino acid
　　　　(D) TOPOLOGY: linear (ii) MOLECULE TYPE: protein (xi) SEQUENCE DESCRIPTION: SEQ ID NO:5:

Arg Thr Lys Arg Ser Gly Ser Val Tyr Glu Pro Leu Lys Thr
1               5                   10

(2) INFORMATION FOR SEQ ID NO:6:

(i) SEQUENCE CHARACTERISTICS:
　　　　(A) LENGTH: 45 base pairs
　　　　(B) TYPE: nucleic acid
　　　　(C) STRANDEDNESS: single
　　　　(D) TOPOLOGY: linear ( i i ) MOLECULE TYPE: DNA (genomic)

( x i ) SEQUENCE DESCRIPTION: SEQ ID NO:6:

CACCTAATAC GACTCACTAT AGGGAGAATG GAAGACGCCA AAAAC  45

( 2 ) INFORMATION FOR SEQ ID NO:7:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:7:

AGAACTGCCT GCCGCAGATT CTCGCA  26

( 2 ) INFORMATION FOR SEQ ID NO:8:

( i ) SEQUENCE CHARACTERISTICS:
      ( A ) LENGTH: 59 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:8:

ATGCTGTCCC GGCTGTCCCT GCGGCTGCTG TCCCGGTACC TGCTGAAGAC GCCAAAAAC  59

( 2 ) INFORMATION FOR SEQ ID NO:9:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:9:

CACCTAATAC GACTCACTAT AGGGAGAATG CTGTCCCGGC TGTCC  45

( 2 ) INFORMATION FOR SEQ ID NO:10:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

TCTCGCTGAA TACAGTTAC  19

( 2 ) INFORMATION FOR SEQ ID NO:11:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

CCCCAAGCTT AGATCTCTCT GATTTTCTT GCGT  34

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
TGCGAGAATC TGCGGCAGGC AGTTCT                               26
```

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Arg  Arg  Xaa  Ser
 1
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Arg  Thr  Lys  Arg  Ser  Gly  Ser  Val  Tyr  Glu  Pro  Leu  Lys  Ile
 1                  5                        10
```

( 2 ) INFORMATION FOR SEQ ID NO:15:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
TAATACGACT CACTATAGGG GAGAGAATGG TCAAGCTTTA CATCAGACTT CGAC       54
```

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GAATTCTTAG GGGACAGCTC CACCGTA                              27
```

( 2 ) INFORMATION FOR SEQ ID NO:17:

( i ) SEQUENCE CHARACTERISTICS:

-continued ( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

GCTCGTCTTA TTGAAGATAA TGAATATACT GCTCGTTTTG GT        42